United States Patent [19]

Dirlam et al.

[11] Patent Number: 5,350,764
[45] Date of Patent: Sep. 27, 1994

[54] ANTICOCCIDIAL AND GROWTH PROMOTING POLYCYCLIC ETHER ANTIBIOTIC

[75] Inventors: John P. Dirlam, Gales Ferry, Conn.; Hiroshi Maeda; Junsuke Tone, both of Chita, Japan

[73] Assignee: Pfizer Inc., New York, N.Y.

[21] Appl. No.: 30,055

[22] Filed: Mar. 12, 1993

Related U.S. Application Data

[63] Continuation of Ser. No. 590,891, Oct. 1, 1990, abandoned.

[51] Int. Cl.$^5$ .................. A61K 31/35; C07D 315/00
[52] U.S. Cl. .................................. 514/460; 549/414
[58] Field of Search .......................... 549/414; 514/460

[56] References Cited

U.S. PATENT DOCUMENTS

| | | | |
|---|---|---|---|
| Re. 29,651 | 5/1978 | Stempel et al. | 549/414 |
| 3,944,573 | 3/1976 | Westley | 549/414 |
| 4,168,272 | 9/1979 | Westley | 549/414 |
| 4,193,928 | 3/1980 | Coffen | 549/414 |

OTHER PUBLICATIONS

Westley et al., *J. Antibiotics,* 27, 744–53 (1974).

*Primary Examiner*—Nicky Chan
*Attorney, Agent, or Firm*—Peter C. Richardson; Gregg C. Benson; Robert T. Ronau

[57] ABSTRACT

An acidic polycyclic ether antibiotic, having structure established by X-ray crystallography, is formed by fermentation of a novel microorganism, Actinomadura sp. ATCC 55027. This novel antibiotic is useful as an anticoccidial in poultry, in the prevention and treatment of swine dysentery and as a growth promotant in cattle and swine.

11 Claims, No Drawings

ANTICOCCIDIAL AND GROWTH PROMOTING POLYCYCLIC ETHER ANTIBIOTIC

CROSS REFERENCE TO RELATED APPLICATIONS

This application is a continuation of International Application PCT/US91/06085, filed Aug. 30, 1991, designating the United States, entitled "Anticoccidial and Growth Promoting Polycyclic Ether Antibiotic," which is a continuation of U.S. application Ser. No. 07/590,891, filed Oct. 1, 1990, entitled "Anticoccidial and Growth Promotant Polycyclic Ether Antibiotic" (now abandoned).

BACKGROUND OF THE INVENTION

The present invention concerns a new acidic polycyclic ether antibiotic having the formula:

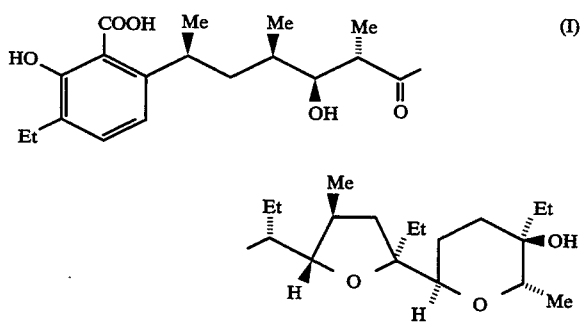

having relative stereochemistry as shown; pharmaceutically acceptable cationic salts thereof; nutrient feed compositions comprising said antibiotic for poultry, cattle or swine; its use as an anticoccidial agent in poultry, in the treatment or prevention of swine dysentery, or as a growth promotant in cattle or swine; a fermentation method for its preparation; and the Streptomyces sp. microorganism which produces said antibiotic in said fermentation method.

The compound (I) is a new member of the acidic polycyclic ether group of antibiotics. This family includes such well known agents as monensin (The Merck Index, 11th Ed., Merck and Co., Inc., Rahway, N.J., 1989, Monograph no. 6157), nigericin (loc. cit., monograph no. 6457), narasin (loc. cit., monograph no. 6339), and the lasalocids A-E (Westley et al., J. Antibiotics, vol. 27, p. 744, 1974), with lasalocid B possessing a structure particularly close to that of the compound (I).

A culture of Streptomyces sp., ATCC 55027, when fermented under aerobic conditions in aqueous media, produces a new acidic polycyclic ether antibiotic, a compound having the formula (I), as specified above.

The present invention is directed to said compound of the formula (I), including the pharmaceutically-acceptable cationic salts thereof, and to a process for its preparation which comprises fermentation of said Streptomyces sp. ATCC 55027 in an aqueous nutrient medium comprising an assimilable source of carbon and nitrogen until a recoverable amount of said compound of the formula (I) is formed, preferably under submerged aerobic conditions. For use as an anticoccidial agents, in the prevention or treatment of swine dysentery, and/or as a growth promotant, the compound (I) can be separated from the fermentation and isolated in substantially pure form. However, it is alternatively used in crude form, either in precipitated form admixed with mycelium (recovered by filtration of the fermentation medium), or in solids obtained by spray—or freeze-drying the entire fermentation medium.

Said pharmaceutically-acceptable cationic salts include, but are not limited to those of sodium, potassium, calcium, ammonia, N,N'-dibenzylethylenediamine, N-Methylglucamine (meglumine) and diethanolamine. The preferred cationic salts are those of potassium and sodium.

The present invention is also directed to nutrient feed compositions, one for cattle or swine which comprises the compound of the formula (I) in an amount effective to promote and/or improve the feed utilization of said cattle or swine, or to prevent or treat dysentery in swine; and the other for poultry which comprises the compound of the formula (I) in an amount effective to control coccidial infection in said poultry.

The present invention is further directed to a method for promoting growth and/or increasing the efficiency of feed utilization in swine or cattle which comprises administering to said swine or cattle a growth promoting or feed-utilization efficiency promoting amount of the compound of the formula (I), particularly in the form of a nutrient feed composition; to a method for preventing or treating dysentery in swine which comprises administering to said swine a compound of the formula (I) in an amount effective in preventing or treating said dysentery in said swine; and to a method for controlling coccidial infections in poultry which comprises administering to said poultry an anticoccidially effective amount of the compound of the formula (I), particularly in the form of a nutrient feed composition.

Finally, the present invention is directed to a biologically pure culture of Streptomyces sp. ATCC 55027, said culture being capable of producing the compound of the formula (I) in a recoverable quantity upon fermentation in an aqueous medium comprising assimilable sources of carbon and nitrogen; including said culture in freeze-dried form.

DETAILED DESCRIPTION OF THE INVENTION

The culture capable of producing the present polycyclic ether antibiotic of the formula (I) is designated Streptomyces sp., and has been deposited under the Budapest treaty in The American Type Culture Collection, Rockville, Md. as the type culture under the accession number ATCC 55027. Permanency of the deposit of this culture at The American Type Culture Collection at Rockville, Md. and ready accessibility thereto by the public are afforded throughout the effective life of the patent.

This novel culture was derived from a soil sample collected in Tsukuba Town, Ibargi Prefecture, Japan; and identified in the culture collections of Pfizer Inc. as N768-28 and as F.D. 28706. Its description and classification were provided by Dr. L. H. Huang. This culture was found to produce narrow dimensions of the hyphae typical of the Actinomycetales, an aerial mycelium upon which spore chains are produced, and an unfragmented substrate mycelium. The results of the whole cell analyses further indicated that it belongs to the genus Streptomyces.

A slant culture of the microorganism on ATCC 172 media was inoculated into ATCC 172 broth and grown for four days at 28 C. on a shaker. It was then centrifuged for 20 minutes, washed three times with sterile distilled water, and planted on media commonly used for identification of members of the Actinomycetales.

The cultures were incubated at 28 C. and the results read at varying times, but most commonly at fourteen days. The colors were described in common terminology, but exact colors were determined by comparisons with color chips from *The Color Harmony Manual*, fourth edition. The methods of whole-cell amino acid and sugar analyses are those described in Backer at al., Appl. Microbiol., vol. 12, pp. 421–423 (1964), and in Lechevalier, J. Lab. Clin. Med., Vol. 71, pp. 934–944 (1968), respectively.

The culture was identified as follows:

Yeast Extract-Malt Extract Agar (ISP #2 medium, Difco)—Growth good; cream (2 ca); raised, wrinkled; aerial mycelium sparse, white; reverse pale yellowish (2 ga, 2 ic); no soluble pigment.

Oatmeal Agar (ISP #3 medium, Difco)—Growth moderate, white to cream (1½ ca); slightly raised, smooth, with white aerial mycelium; reverse pale yellowish (2 ca, 2 ea); soluble pigment cream (2 ca).

Inorganic Salts-Starch Agar (ISP #4 medium, Difco)—Growth poor to moderate; white to cream (2 ca); slightly raised, smooth, confluent or appearing as isolated colonies, with white aerial mycelium; reverse pale yellowish (2 ea, 2 ca); no soluble pigment.

Glycerol-Asparagine Agar (ISP #5 medium, Difco)—Growth poor to moderate; white to cream (2 ca); slightly raised, smooth, confluent or appearing as isolated colonies; aerial mycelium white; reverse colorless to cream (1½ ca); no soluble pigment.

Czapek-Sucrose Agar (Waksman, "The Actinomycetes", v. 2, medium #1, p. 328, 1961)—Growth moderate; white; slightly raised, smooth; aerial mycelium white; reverse colorless; no soluble pigment.

Glucose-Asparagine Agar (ibid., medium #2)—Growth moderate to good; cream with a white edge; thin to slightly raised, smooth to slightly wrinkled; aerial mycelium white; reverse cream to pale yellowish (2 ca, 2 ea); no soluble pigment.

Gordon and Smith's Tyrosine Agar (Gordon and Smith, J. Bacteriol., 69:147–150, 1955)—Growth moderate; white to cream (2 ca); thin to slightly raised, smooth, with white aerial mycelium; reverse cream to pale yellowish (2 ca, 2 ea); no soluble pigment.

Calcium Malate Agar (Waksman, Bacteriol. Rev., 21, 1–29, 1957)—Growth moderate; white; thin to slightly raised, smooth, with white aerial mycelium; reverse colorless to cream (2 ca); no soluble pigment.

Casein Agar (Gordon and Smith, ibid.)—Growth moderate; cream (2 ca); slightly raised, smooth but wrinkled toward end of streak, with no aerial mycelium; reverse pale yellowish (2 ea); soluble pigment yellowish (2 ia).

Bennett's Agar (Waksman, loc. cit., medium #30, p. 331)—Growth good; white to cream (2 ca); moderately raised, wrinkled; aerial mycelium white; reverse pale yellowish (2 ea, 2 ga); soluble pigment pale yellowish (2 ea).

Emerson's Agar (ibid, medium #28, p. 331)—Growth good; dark cream (2 gc); raised, wrinkled; no aerial mycelium; reverse same as surface; soluble pigment yellowish (2 lc).

Nutrient Agar (ibid., medium #14, p. 330)—Growth moderate; cream (2 ca, 2 ea); thin to slightly raised, smooth, aerial mycelium none to sparse white; reverse colorless to cream (2 ca); no soluble pigment.

Gelatin Agar (Gordon and Mihm, J. Bacteriol., 73, 15–27, 1957)—Growth moderate to good; white; moderately raised, smooth, with white aerial mycelium; reverse cream (2 ca); no soluble pigment.

Starch Agar (ibid.)—Growth moderate to good; white; moderately raised, smooth, with white aerial mycelium; reverse cream to pale yellowish (2 ca, 2 ea); no soluble pigment.

Potato Carrot Agar (Lechevalier, Lab. Clin. Med., 71, 934–944, 1968, but use only 30 g. potatoes, 2.5 g. carrots and 20 g. agar)—No growth.

Tap Water Agar (2%)—Growth moderate; white; moderately raised, smooth; aerial mycelium white; reverse colorless; no soluble pigment.

Morphological Properties—The morphological properties were observed after 16 days of incubation on oatmeal agar: spore mass in white color-series; spore chains in Section Rectiflexibiles, straight, curved or irregularly flexuous; 10 to 50 or more than 50 spores per spore chain; sporophores monopodially branched; spores rod-shaped, sometimes oval to elliptical, 1–2×0-.6–1.0 μm or longer; smooth, as revealed by scanning electron microscopy.

Biochemical Properties—Melanin not produced; hydrogen sulfide not produced; gelatin liquefied; starch hydrolyzed; nitrate not reduced to nitrite; no growth and no decomposition on Jensen's cellulose broth or Levine and Schoelein's cellulose broth; peptonization and coagulation of milk; casein digestion positive; tyrosine digestion negative; calcium malate digestion negative. Carbohydrate utilization: glucose, sucrose, fructose, mannitol, raffinose, sucrose, and xylose utilized; arabinose, inositol and rhamnose not utilized.

| | Temperature Relations - | | |
|---|---|---|---|
| 21° C. | 28° C. | 37° C. | 45° C. |
| Good Growth | Good Growth | No Growth | No Growth |

Cell Wall Analysis—The whole-cell hydrolysates contained LL-diaminopimelic acid, and no diagnostic sugars.

The present culture is characterized by the white spores in mass, the negative melanin reaction, the straight to flexuous spore chains, and the smooth spores. The whole-cell hydrolysates indicate the presence of LL-diaminopimelic acid and the absence of diagnostic sugars. Glucose, fructose, mannitol, raffinose, sucrose, and xylose were utilized. Thus, the culture belongs to the genus Streptomyces.

When compared with known species of Streptomyces, the present culture resembles *S. albosporeus* (Krainsky) Waksman and Henrici subsp. labilomyceticus Okami, Suzuki and Umezawa (J. Antibiotic Series A 16:152–154, 1963) in cultural, morphological and biochemical properties. However, it differs from the latter in the cream rather than the pale brown to pale pink vegetativegrowth on some media, and in the positive utilization of fructose.

On the basis of the data presented above, the present culture N768-28 is considered as a new strain of the genus Streptomyces and designated Streptomyces sp. It has been deposited with The American Type Culture Collection under the accession number ATCC 55027.

The antibiotic compound (I) of the present invention is readily produced by the present Streptomyces sp. by growing at from about 20 degrees to about 35 degrees C. under submerged conditions with agitation and aeration on media consisting of carbohydrate sources such as sugars, starches, glycerol; organic nitrogen substances such as soybean meal, casamino acids, yeast extract; growth substances such as grain solubles, fish meal, cotton seed meal; mineral salts containing trace elements such as iron, cobalt, copper, zinc, etc.; and calcium carbonates or phosphates as buffering agents. After growth has been completed, the antibiotic is readily recovered by extracting the whole broth with an organic solvent such as n-butanol, methylisobutyl ketone, or chloroform at pH ranges from 4.0 to 8.0; by filtering off the mycelium, which contains the precipitated antibiotic, the filtrate being discarded; or by simply spray-drying or freeze-drying the whole broth. Alternatively, the mycelium or the whole dried broth is extracted with one of said organic solvents. The purified antibiotic compound, if that is desired, is isolated from the organic extract by standard methods of concentration, salt or free acid formation, chromatography, precipitation and/or crystallization, as exemplified below.

In the usual manner of carrying out the fermentation, an inoculum is first prepared by scraping vegetative cells, growing on a suitable media, from slants or Roux bottles which have been inoculated with Streptomyces sp. ATCC 55027. The resulting vegetative cells are in turn used to inoculate shake flasks or inoculum tanks, also containing suitable growth media. Alternatively, the inoculum tanks are inoculated from the shake flasks. Following a suitable growth period (generally 120 to 144 hours in shake flasks and 168 to 196 hours in inoculum tanks), a fermenter, also containing suitable growth media, is inoculated under aseptic conditions with vegetative broth from the shake flasks or inoculum tanks. Upon completion of growth (generally about 120-196 hours), the antibiotic compound is recovered in crude or pure form, as desired, by one or another of the methods generally described above, or by specific methods which are exemplified below.

The compound of the formula (I) is tested for in vitro antibacterial activity by standard methods in which the minimum inhibitory concentrations (MIC'S) in mcg/ml against one or more microorganisms is measured. One such procedure is the one recommended by the International Collaborative Study on Antibiotic Sensitivity Testing (Ericcson and Sherris, Acta. *Pathologica et Microbiologia Scandinav*, Supp. 217, Section B: 64-68 [1971]), and employs brain heart infusion (BHI) agar and an inocula replicating device. Overnight growth tubes are diluted 100 fold for use as the standard inoculum (20,000-100,000 cells in approximately 0.002 ml. are placed on the agar surface; 20 ml. of BHI agar/dish). Twelve 2 fold dilutions of the test compound are employed, with initial concentration of the test drug being 200 mcg/ml. Single colonies are disregarded when reading plates after 18 hours at 37 degrees C. The susceptibility (MIC) of the test organism is accepted as the lowest concentration of compound capable of producing complete inhibition growth as judged by the naked eye. Like other polycyclic ether antibiotics, the present compound of the formula (I) typically shows Gram positive antibacterial activity, as well as activity against *Treponema hyodysenteriae* (the causative agent of swine dysentery).

Efficacy data for the compound of the formula (I) and its salts against coccidial infections in chickens is obtained by the following method. Groups of 3-5 ten-day old pathogen free white leghorn cockerel chicks are fed a mash diet containing the compound (I) or its sodium and/or potassium salt uniformly dispersed therein. After being on this ration for 24 hours each chick is inoculated per os with oocysts of the particular species of Eimeria being tested. Other groups of 3-5 ten-day old chicks are fed a similar mash diet without compound (I) or its salts. They are also infected after 24 hours and serve as infected controls. Yet another group of 3-5 ten-day old chicks are fed the same mash diet without antibiotic and are not infected with coccidia. These serve as normal controls. The results of treatment are evaluated after five days in the case od E. acervulina, and six days for all other challenges.

The criteria used to measure anticoccidial activity consists of lesion scores of 0 to 4 for *E. tenella* after J. E. Lynch, "A New Method of the Primary Evaluation of Anticoccidial Activity", *Am. J. Vet. Res.*, 22, 324-326, 1961; and 0 to 3 for the other species based on modification of the scoring system devised by J. Johnson and W. H. Reid, "Anticoccidial Drugs. Lesion Scoring Techniques in Battery and Floor Pen Experiments in Chicks", *Exp. Parasit.*, 28, 30-36, 1970. Activity is measured by dividing the lesion score of each treated group by the lesion score of the infected control. In this test, for example, the compound (I) and its cationic salts exhibit activity against *Eimeria tenella*, infections in poultry when incorporated into the mash diet of chickens at levels of about 30 to 60 ppm. The present compound of the formula (I) is also generally useful in combination with certain other known anticoccidial agents, such as nicarbazin, 4,4'-dinitrocarbanilide or a napthalenamine, as defined by Hamill et al., U.S. Pat. No. 4,582,822.

For the prevention or control of coccidiosis in poultry, the compound of this invention is orally administered to poultry in a suitable carrier. Conventionally, the medication is simply carried in the drinking water or in the poultry feed, so that a therapeutic dosage of the agent is ingested with the daily water or poultry ration. The agent can be directly metered into drinking water, preferably in the form of a liquid concentrate; or added directly to the feed as such, or, more commonly, added to the feed in the form of a premix or concentrate of therapeutic agent in a solid carrier. The therapeutic agent can be in substantially pure form (e.g., the free acid, or a pharmaceutically-acceptable salt thereof), or in assayed crude form such as wet or dry mycelium or dried whole broth. Suitable carriers are liquid or solid, as desired, such as water, various meals (for example), soybean oil meal, linseed oil meal, corncob meal) and mineral mixes such as are commonly employed in poultry feeds. A particularly effective carrier is the poultry feed itself; that is, a small portion of poultry feed. The carrier facilitates uniform distribution of the active materials in the finished feed with which the premix is blended. This is important because only small proportions of the present potent agents are required. It is important that the compound be thoroughly blended into the premix and, subsequently, into the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variations since the amount of agent in the finished feed may be adjusted by blending the appropriate proportion of premix with the feed to obtain a desired level of therapeutic agent.

High potency concentrates are blended by the feed manufacturer with proteinaceous carrier such as soybean oil meal and other meals, as described above, to produce concentrated supplements which are suitable for direct feeding to poultry. In such instances, the poultry are permitted to consume the usual diet. Alternatively, such concentrated supplements are added directly to the poultry feed to produce a nutritionally balanced, finished feed containing a therapeutically effective level of the compound of this invention. The mixtures are thoroughly blended by standard procedures, such as in a twin shell blender, to ensure homogeneity. For use in poultry, use levels of the compound described herein will vary under different circumstances. Continuous low-level medication, during the growing period; that is, during the first 5 to 12 weeks for chickens, is an effective prophylatic measure. In the treatment of established infections, higher levels may be necessary to overcome the infection. The use level of the compound (I) in feed will generally be in the range of about 10 to 100 ppm. When administered in drinking water, the level which will be that which will provide the same daily dose of medication factored by the weight ratio of the average daily consumption of feed to the average daily consumption of water.

The activity of the compound of the formula (I) and its salts in the promotion of growth and/or increasing the efficiency of food utilization in swine or cattle can be measured directly by feeding test groups of animals various levels of the compound (I) or a salt in feed. Alternatively, British Patent Specifications No. 1,197,826 details an in vitro rumen method for the evaluation of antibiotics in feeds.

For use in the prevention or treatment of swine dysentery, or in promoting growth and/or increasing the efficiency of feed utilization in cattle or swine the compound of the formula (I) or a salt is preferably administered as a feed additive. The feeds prepared according to methods fully analogous to those detailed above for the preparation of poultry feed, with the same concern for producing feeds in which the therapeutic agent is uniformly dispersed. The use level of the compound (I) in cattle or swine feed will generally be in the range of about 10 to 100 ppm. In ruminants the compound of the formula (I) can also be orally administered in the form of a bolus which is retained in the rumenoreticular sac, releasing the therapeutic agent at a substantially constant rate ever a prolonged period of time, e.g., 4–8 weeks, providing a dose equivalent to that of the above daily dose in feed, i.e.:

$$\frac{\text{average daily dose in milligrams}}{} = \frac{10 \text{ to } 100}{\text{ppm}} \times \text{average daily feed consumption in Kg.}$$

The present invention is illustrated by the following examples. However, it should be understood that the invention is not limited to the specific details of these examples.

EXAMPLE 1

Fermentation of Streptomyces sp. ATCC 55027 Isolation of the Antibiotic of the Formula (I) as Sodium Salt The Streptomyces species was initially grown on slants inoculated with ATCC 55027 culture. A potion of the slant was used to inoculate 150 ml. of the following medium:

| W | |
|---|---|
| Glucose | 1 |
| Dextrin | 24 |
| Polypeptone | 5 |
| Yeast extract | 5 |
| Beef extract | 3 |
| $CaCO_3$ | 4 | in a stirred 500 ml. flask (minijar). This was fermented at 28 degrees C. for 3.5 days at 200 rpm and in turn used to seed 3 liters of one of the following media:

| JA | | MECO | |
|---|---|---|---|
| Composition | (g/l) | Composition | (g/l) |
| Glucose | 10 | Glucose | 10 |
| Dextrin | 5 | Corn starch | 20 |
| Corn steep liquor | 5 | NZ Amine type-A | 5 |
| Blood meal | 5 | Yeast extract | 5 |
| $CaCO_3$ | 3 | Wheat embryo | 5 |
| | | $CoCl_2 6H_2O$ | 0.001 |
| | | $CaCO_3$ | 4 |

| C-4 | | IT-2 | |
|---|---|---|---|
| Composition | (g/l) | Composition | (g/l) |
| Glucose | 20 | Glucose | 10 |
| Glycerol | 10 | Dextrin | 20 |
| Soybean meal | 10 | Wheat gluten | 10 |
| Corn steep liquor | 10 | Corn steep liquor | 5 |
| $Na_2SO_4$ | 0.5 | Polypetone | 1 |
| $CoCl_2 6H_2O$ | 0.001 | $(NH_4)_2SO_4$ | 1 |
| $CaCO_3$ | 4 | $CoCl_2 6H_2O$ | 0.001 |
| | | $CaCO_3$ | 4 | in 6 liter sterile fermentation flasks. These main fermentations were carried out at 28 degrees C. for 4 days at 1700 rpm and aerated with one volume of air per volume of liquid per minute. The completed fermentations were clarified by filtration over diatomaceous earth and the antibiotic isolated from the filtrate as detailed below.

Broth (80 liters) prepared according to the preceding paragraph was extracted with methylisobutyl ketone at natural pH. The organic extract was concentrated under vacuum to afford an oily residue. The residue was chromatographed using 300 g of column grade silica gel, 32–63 microns, employing a gradient of 80:20 to 50:50 hexane:ethyl acetate. The eluates were examined by thin layer chromatography (tlc) on silica gel plates developed with chloroform:isopropanol (95:5), then sprayed with 3.3% vanillin dissolved in ethanol:phosphoric acid (2:1), and heated to 80 degrees C. Fractions with common components were combined and tested for antibacterial activity against Staphylococcus aureus 01A110. Active fractions were combined, and were further purified by flash chromatography using a column of 100 g of silica gelutilizing a gradient of 90:10 hexane:ethyl acetate to 100% ethyl acetate. Again, the eluates were examined by tlc. After spraying with vanillin indicator and heating to 80 degrees C., the active component appeared as a yellow spot Rf 0.32. All fractions containing this component were combined and chromatographed using flash column chromatography (100 g of silica gel; 80:20 chloroform:ethyl acetate) and 387 mg of sodium salt of the compound of formula (I)

was obtained following the removal of solvent under vacuum: mp 160°-162° degrees C., $[\alpha]_D^{25} = -44.3$ degrees (c=1, CH$_3$OH).

The structure of the compound of formula (I) was assigned based on $^{13}$C and $^1$H NMR (including $^{13}$C DEPT, HETCOR and long-range $^{13}$C-$^1$H coupling experiments) and mass spectral data. The relative stereochemistry was determined by X-ray analysis of the Cs salt of I. However, the X-ray data were inconclusive regarding the carbon chain-length at the 4-position of the aromatic ring (i.e., methyl or ethyl), and the 4-ethyl assignment was made based on NMR data. Spectroscopic data and elemental analysis were consistent with C$_{36}$H$_{57}$O$_8$Na for the sodium salt of I. For example, in the positive FAB-MS, diagnostic cationized molecules m/z 641 (m+Na)$^+$ and 663 (M+2Na—H)$^+$ were detected for compound (I) as the sodium salt.

Anal Calcd. for C$_{36}$H$_{57}$O$_8$NaH$_2$O:C, 65.60; H, 8.99 Found: C, 64.92; H, 8.68. $^{13}$C NMR [chemical shift (ppm) in CDCl$_3$ with number of hydrogens in parenthesis]: 216.18 (0), 176.16 (0), 158.73 (0), 149.97 (0), 129.87 (1), 128.26 (0), 118.30 (0), 115.39 (1), 86.77 (0), 82.72 (1), 76.04 (1), 71.01 (0), 69.78 (1), 69.30 (1), 55.83 (1), 48.46 (1), 44.60 (2), 38.00 (2), 34.35 (1), 31.46 (2), 31.02 (1), 30.55 (1), 29.68 (2), 29.56 (2), 23.18 (2), 18.98 (2), 18.66 (3), 15.46 (2), 15.36 (3), 14.01 (3), 13.27 (3), 13.27 (3), 12.41 (3), 12.41 (3), 9.21 (3) and 6.41 (3).

IR (film) cm$^{-1}$: 1700 (ketone) and 1585 (carboxylate).

UV (methanol): inflection at 246 nm, maximum at 305 nm.

EXAMPLE 2

Compound (I) in the Free Acid Form

The free acid form of the antibiotic of the formula (I) was prepared by vigorously shaking a chloroform solution of the sodium salt with an equal volume of hydrochloric acid at pH 3 in a separatory funnel. The phases were separated, and the chloroform layer was washed with water and then evaporated under vacuum to give the free acid.

IR (film) cm$^{-1}$: 1700 (ketone) and 1645 (hydrogen-bonded carboxyl group).

EXAMPLE 3

The Cesium Salt of the Compound (I)

To prepare the cesium salt of the compound of the formula (I), the free acid (98 mg) was dissolved in 70 ml of chloroform. Cesium carbonate (130 mg in 100 ml of water) was added and the resulting mixture stirred for several minutes and was then placed in a separatory funnel and vigorously shaken for several minutes. The organic phase was separated and evaporated under vacuum to afford a white solid. The cesium salt was recrystallized by slow evaporation from methylene chloride:heptane (2:1) and X-ray data was obtained from the resulting crystals by Ms. G. Schulte.

We claim:

1. A compound of the formula

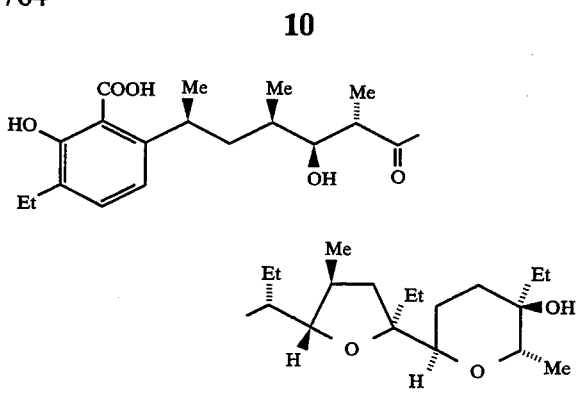

or a pharmaceutically acceptable cationic salt thereof, wherein Me represents CH$_3$ and Et represents CH$_2$CH$_3$.

2. The compound of claim 1 in the form of a sodium or potassium salt.

3. A nutrient feed composition for cattle comprising a compound according to claim 1 in an amount effective in promoting growth or improving feed utilization efficiency in cattle.

4. A nutrient feed composition for swine comprising a compound according to claim 1 in an amount effective in preventing or treating dysentery, in promoting growth or in improving feed utilization efficiency in swine.

5. A nutrient feed composition for poultry comprising a compound according to claim 1 in an amount effective in preventing or controlling coccidial infections in poultry.

6. A method for promoting growth or increasing the efficiency of feed utilization in cattle comprising administering to said cattle a compound according to claim 1 in an amount effective in promoting growth or increasing feed utilization efficiency in cattle.

7. A method for promoting growth or increasing the efficiency of feed utilization in cattle comprising administering to said cattle a nutrient feed composition according to claim 3.

8. A method for preventing or treating dysentery, promoting growth or improving feed utilization efficiency in swine comprising administering to said swine a compound according to claim 1 in an amount effective in preventing or treating dysentery, promoting growth or increasing the efficiency of feed utilization in said swine.

9. A method for preventing or treating dysentery, promoting growth or improving feed utilization efficiency in swine comprising administering to said swine a nutrient feed composition according to claim 4.

10. A method for preventing or controlling coccidial infections in poultry comprising administering to said poultry a compound according to claim 1 in an amount effective in preventing or controlling coccidial infections in poultry.

11. A method for preventing or controlling coccidial infections in poultry comprising administering to said poultry a nutrient feed composition according to claim 5.

* * * * *